(12) United States Patent
Lee et al.

(10) Patent No.: US 10,342,835 B2
(45) Date of Patent: Jul. 9, 2019

(54) COMPOSITION CONTAINING ANGELICA EXTRACT FOR PROMOTING PROLIFERATION OF STEM CELLS DERIVED FROM BONE MARROW

(71) Applicant: COMPREHENSIVE AND INTEGRATIVE MEDICINE INSTITUTE, Daegu (KR)

(72) Inventors: Chang Hyeong Lee, Daegu (KR); Sang Gyung Kim, Daegu (KR); Im Hee Shin, Daegu (KR); Seung Mo Kim, Daegu (KR); Joon Seok Byun, Daegu (KR); Ki Cheul Sohn, Daegu (KR); Sae Kwang Ku, Daegu (KR)

(73) Assignee: COMPREHENSIVE AND INTEGRATIVE MEDICINE INSTITUTE, Daegu (KR)

( * ) Notice: Subject to any disclaimer, the term of this patent is extended or adjusted under 35 U.S.C. 154(b) by 0 days.

(21) Appl. No.: 15/969,762

(22) Filed: May 2, 2018

(65) Prior Publication Data

US 2018/0243358 A1   Aug. 30, 2018

Related U.S. Application Data

(63) Continuation of application No. 14/888,682, filed as application No. PCT/KR2014/003910 on May 1, 2014, now abandoned.

(30) Foreign Application Priority Data

May 3, 2013   (KR) ........................ 10-2013-0050337

(51) Int. Cl.
*A61K 38/19*   (2006.01)
*A61K 36/232*   (2006.01)

(52) U.S. Cl.
CPC .......... *A61K 36/232* (2013.01); *A61K 38/193* (2013.01)

(58) Field of Classification Search
None
See application file for complete search history.

(56) References Cited

U.S. PATENT DOCUMENTS 6,964,785 B2   11/2005   Jo et al.

FOREIGN PATENT DOCUMENTS

| EP | 1466608 B1 | 4/2006 |
| KR | 10-2009-0126692 A | 12/2009 |
| KR | 10-2010-0008541 A | 1/2010 |
| KR | 10-2010-0018278 A | 2/2010 |
| KR | 10-1077042 81 | 10/2011 |

OTHER PUBLICATIONS

Morrison et al., "Cyclophosphamide/granulocyte colony-stimulating factor induces hematopoietic stem cells to proliferate prior to mobilization", PNAS, 1997, vol. 94, pp. 1908-1913.
International Search Report and Written Opinion for International Application No. PCT/KR2014/003910 (7 Pages) (dated Sep. 4, 2014).

*Primary Examiner* — Michael Barker
(74) *Attorney, Agent, or Firm* — Lucas & Mercanti, LLP

(57) ABSTRACT

The present invention relates to a composition for promoting proliferation of bone marrow derived stem cells using an angelicae gigantis radix extract, and more particularly, to a composition which administers a granulocyte colony-stimulating factor into an object, and administers the angelicae gigantis radix extract to the object to promote the proliferation of the bone marrow derived stem cells. The composition of the present invention solves side effects such as splenomegaly which were caused by a method of administering only the G-CSF for proliferation and differentiation of the stem cells, thereby significantly mitigating the side effects through co-administration of the angelicae gigantis radix extract, and further promoting the proliferation and the differentiation of the stem cells.

4 Claims, 18 Drawing Sheets

COMPOSITION CONTAINING ANGELICA EXTRACT FOR PROMOTING PROLIFERATION OF STEM CELLS DERIVED FROM BONE MARROW

CROSS-REFERENCE TO RELATED APPLICATIONS

This application is a continuation of U.S. patent application Ser. No. 14/888,682 filed Nov. 2, 2015, which is a 371 of PCT/KR2014/003910, filed May 1, 2014, which claims the benefit of Korean Patent Application No. 10-2013-0050337, filed May 3, 2013, the contents of each of which are incorporated herein by reference.

TECHNICAL FIELD

The present invention provides a composition containing an angelicae gigantis radix extract for promoting proliferation of bone marrow derived stem cells.

BACKGROUND ART

"Stem cell" is a generic term for undifferentiated cells that can differentiate into various cells forming biological tissues and obtained from tissue of embryos, fetuses, and adults. Among various stem cells, adult stem cells are cells derived from bone marrow, and are multifunctional stem cells which can be differentiated into any cell forming an organ and blood of a human body.

Among these, bone marrow derived stem cells are considered as an ultimate means of treating diseases such as hematologic cancers, lymphoma, and bone marrow failure. Transplantation of bone marrow derived stem cells is currently being performed for various purposes, and particularly when organ transplantation is difficult in critical kidney and liver patients, a method of promoting regeneration of the liver and kidneys is being attempted by transplanting autologous bone marrow derived stem cells.

After the autologous bone marrow derived stem cells are transplanted, to promote differentiation and division of the stem cells, a recombinant human granulocyte colony-stimulating factor (hG-CSF) is administered in full dose. However, in about 5-30% of patients, proliferation or mobilization toward blood does not occur in the stem cells, and various side effects such as myocardial infarction, cerebral infarction, fever, ostalgia, splenomegaly, splenic rupture, etc. are known to be caused by the administration of hG-CSF (Masood et al., 2008; Fox et al., 2009). Particularly, the use of hG-CSF is being limited due to its high cost. Consequently, a new alternative means which is capable of promoting an effect of hG-CSF in proliferating the bone marrow derived stem cells, or mitigating the side effects of hG-CSF is required.

Angelicae gigantis radix is a dried substance of roots of *Angelica gigas* NAKAI, *A. sinensis* DIELS, and *A. acutiloba* KITAG, which are perennial herbs belonging to the family Umbelliferae, along with other congeneric, closely-related plants, and is known to have effects of replenishing blood to cure lack of blood supply, reducing menstrual cramps, and moisturizing the intestine to relieve constipation. The roots perform a sedative action, an antispasmodic action, a hypotensive action, etc., and aqueous solutions of essential oils of the roots perform an analgesic action and an anti-inflammatory action when used to treat arthritis. In the field of oriental medicine, the roots are mostly used in anemia, gynecopathy, and postpartum recovery, and are also used for serious coughing, boils, etc. Meanwhile, Korean Unexamined Patent Application Publication No. 2012-0092754 has disclosed content related to promoting differentiation of stem cells using *Chrysanthemum zawadskii*, which is a medicinal herb, but there has been no example of promoting differentiation of "bone marrow derived" stem cells using an angelicae gigantis radix extract.

DISCLOSURE

Technical Problem

The present invention has been devised to resolve the above-mentioned need of the prior art, and is directed to providing a composition for promoting proliferation of bone marrow derived stem cells using an angelicae gigantis radix extract.

However, a technical aspect to be achieved by the present invention is not limited to the above-mentioned aspect, and those of ordinary skill in the art will be able to understand other unmentioned aspects from the description below.

Technical Solution

To achieve the above-mentioned aspect of the present invention, the present invention provides a composition containing a granulocyte colony-stimulating factor and an angelicae gigantis radix extract for promoting proliferation of bone marrow derived stem cells.

According to one embodiment of the present invention, the stimulating factor and the angelicae gigantis radix extract may be mixed in advance and made into a dosage form, or separately made into a dosage form.

According to another embodiment of the present invention, the stimulating factor and the angelicae gigantis radix extract may be administered parenterally, orally, locoregionally, or percutaneously.

According to still another embodiment of the present invention, a period of administering the angelicae gigantis radix extract may begin within thirty minutes after administration of the stimulating factor.

Advantageous Effects

A composition containing an angelicae gigantis radix extract as an effective component for promoting proliferation of stem cells which is provided in the present invention includes a recombinant human granulocyte colony-stimulating factor (hG-CSF) and the angelicae gigantis radix extract, and is administered before transplanting stem cells, thereby promoting proliferation and differentiation of stem cells.

In addition, when the hG-CSF is administered to promote proliferation and differentiation of stem cells and the proliferation of the stem cells is induced, the composition of the present invention may be used as a new alternative means which is able to solve the problem of the prior art which had side effects such as myocardial infarction, cerebral infarction, fever, ostalgia, splenomegaly, splenic rupture, etc.

MODES OF THE INVENTION

Figure 1:
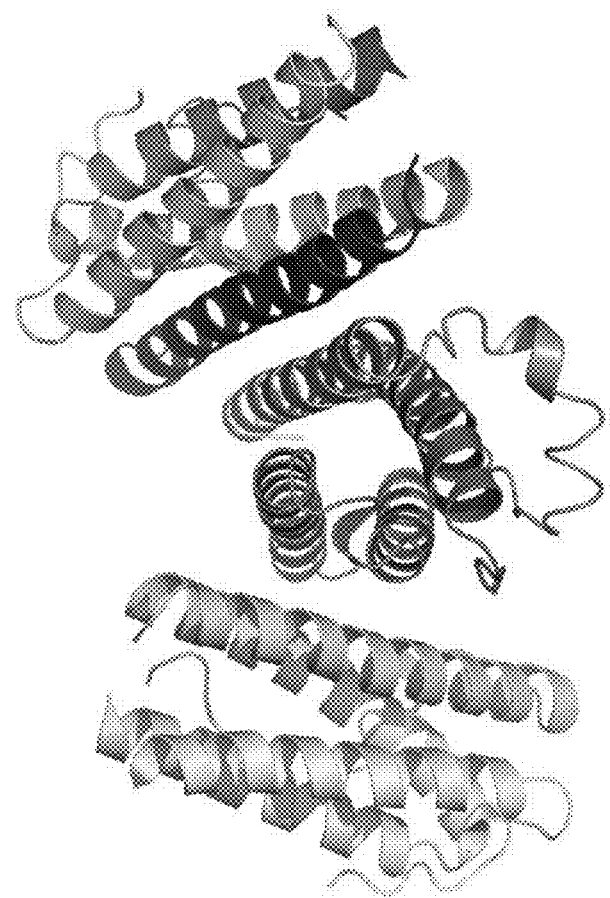
FIG. 1 is a view illustrating a structure of an hG-CSF used in the present invention.

To develop a composition which is capable of mitigating various side effects that occur when the recombinant hG-CSF is administered to promote differentiation and division of bone marrow derived stem cells after the bone marrow derived stem cells are transplanted, and further increasing production of the bone marrow derived stem cells, the present inventors have focused on medicinal herbs, and found that, among the medicinal herbs, angelicae gigantis radix has an outstanding effect in promoting proliferation and differentiation of the stem cells, thus completing the present invention.

Consequently, the present invention is directed to providing a composition containing a G-CSF and an angelicae gigantis radix extract for promoting proliferation of bone marrow derived stem cells.

According to one embodiment of the present invention, the G-CSF and the angelicae gigantis radix extract may be mixed in advance and made into a dosage form, or separately made into a dosage form.

A period of administering the angelicae gigantis radix extract may begin within thirty minutes after administration of the G-CSF, preferably within fifteen minutes, and most preferably within five minutes, but the administration period is not limited thereto.

The G-CSF used in the present invention is the recombinant hG-CSF, but is not limited thereto.

The G-CSF and the angelicae gigantis radix extract may be administered parenterally, orally, locoregionally, or percutaneously. Although it is preferable that the angelicae gigantis radix extract be administered orally, the administration method may be properly selected by those of ordinary skill in the art in accordance with a condition and body weight of a patient, an extent of a disease, a period, etc.

In the present invention, an "individual" refers to an object which requires a treatment of a disease, and more specifically, refers to mammals such as humans or non-human primates, mice, rats, dogs, cats, horses, cattle, etc.

In addition, the present invention may provide a pharmaceutical composition containing the angelicae gigantis radix extract for increasing the production of the bone marrow derived stem cells.

In addition, the composition of the present invention may contain a pharmaceutically acceptable carrier. The pharmaceutically acceptable carrier may include normal saline, polyethylene glycol, ethanol, vegetable oil, isopropyl myristate, etc., but is not limited thereto.

According to an embodiment of the present invention, a preferred administration amount of the pharmaceutical composition varies in accordance with a condition and body weight of a patient, an extent of a disease, a form of a drug, an administration route, and a period, but may be properly selected by those of ordinary skill in the art. However, preferably, the pharmaceutical composition is administered in 0.001 to 300 mg/kg of body weight per day, and more preferably in 0.01 to 200 mg/kg of body weight per day. The pharmaceutical composition of the present invention may be administered to mammals such as rats, mice, livestock, humans, etc. in various routes. The administration methods are not limited, and for example, the pharmaceutical composition of the present invention may be administered orally, rectally, or by intravenous, intramuscular, subcutaneous, intrauterine, or intra cerebroventricular injection.

In the present invention, as a result of orally administering the angelicae gigantis radix extract after administering the hG-CSF, it was confirmed that splenomegaly can be mitigated by orally co-administering the angelicae gigantis radix extract within five minutes after administering the hG-CSF (refer to example 2), spleen weight increase and features of splenomegaly caused by proliferation of nuclear cells in red pulp were significantly ($p<0.01$) suppressed, overall proliferation of granulocytes was unaffected (refer to example 3), and proliferation and mobilization of bone marrow derived stem cells by hG-CSF were significantly ($p<0.01$) increased (refer to example 4).

Consequently, the composition containing the angelicae gigantis radix extract for promoting proliferation of the bone marrow derived stem cells of the present invention is able to increase production of the bone marrow derived stem cells, and mitigate various side effects that were caused before when only a G-CSF was administered.

Hereinafter, preferred embodiments will be provided to assist in understanding of the present invention. However, the following embodiments are provided only to enable easier understanding of the present invention, and the content of the present invention is not limited by the following embodiments.

EMBODIMENTS

In the present embodiments, effects of palmultang, samchulgeonbitang, astragali radix, cervi cornu parvum, and angelicae gigantis radix on medicinal effects and side effects of the hG-CSF, particularly on mobilization of stem cells and splenomegaly, were evaluated using Balb/c mice which are commonly used in the mobilization of stem cells by hG-CSF.

Example 1. Experiment Preparation 1-1. Material Preparation

The hG-CSF was purchased from Life Technologies (Carlsbad, Calif., USA) and used, and a structure thereof is illustrated in FIG. 1.

Palmultang (PMT) was purchased from Hanzung Pharmaceutical Co. Ltd. (Daejeon, Korea) and used, and components thereof and amounts of the components are shown in Table 1 below.

TABLE 1

| Herbs | Scientific Names/Produce Region | Amounts (g) |
| --- | --- | --- |
| Angelicae Gigantis Radix | *Angelica gigas* N. | 2.46 |
| Atractylodis Rhizoma | *Atractylodes ovata* (Thunb.) DC. | 2.46 |
| Cnidii Rhizoma | *Cnidium officinale* Makino | 2.26 |
| Ginseng Radix Alba | *Panax ginseng* C. A. Meyer. | 1.6 |
| Glycyrrhizae Radix | *Glycyrrhiza uralensis* Fisch | 1.8 |
| Hoelen | *Poria cocos* Wolf | 0.13 |
| Paeoniae Radix | *Paeonia lactiflora* Pall. | 1.8 |
| Rehmanniae Radix Preparata | *Rehmannia glutinosa* Liboschitz ex Steudel | 3.33 |
| Total | 8 types | 15.84 |

As medicinal herbs to be compared with an effect of angelicae gigantis radix, PMT, samchulgeonbitang (SCGBT), astragali radix, and cervi cornu parvum were selected and compared. Among the above medicinal herbs, components of SCGBT and amounts of the components are illustrated in Table 2.

TABLE 2

| Herbs | Scientific Names/Produce Region | Amounts (g) |
| --- | --- | --- |
| Amomi Fructus | *Amomum xanthioides* Wallich | 0.16 |
| Atractylodis Rhizoma Alba | *Atractylodes ovata* (Thunb.) DC. | 0.98 |
| Citri Unshii Pericarpium | *Citrus unshiu* S. Marcov. | 0.85 |
| Ginseng Radix Alba | *Panax ginseng* C. A. Meyer. | 0.64 |
| Glycyrrhizae Radix et Rhizoma | *Glycyrrhiza uralensis* Fisch | 0.36 |
| Hawthorn Fruit(Crataegi Fructus) | *Crataegus pinnatifida* Bunge var. typica Schneider | 0.93 |
| Hordei Fructus Germiniatus | *Hordeum vulgare* Linn. | 0.34 |
| Zizyphi Fructus | *Zizyphus jujuba* var. inermis (Bunge) Rehder | 4.17 |
| Magnoliae Cortex | *Magnolia officinalis* Rehder et Wilson | 0.21 |
| Massa Medicata Fermentata | *Triticum aestivum* L. | 0.67 |
| Paeoniae Radix | *Paeonia lactiflora* Pall. | 0.54 |
| Ponciri Fructus | *Poncirus trifoliata* | 0.58 |
| Hoelen | *Poria cocos* Wolf | 0.05 |
| Zingiberis Rhizoma Crudus | *Zingiber officinale* Roscoe | 0.26 |
| Total | 14 types | 10.74 |

1-2. Experimental Animal Preparation

In the present example, Balb/c CrSlc mice (6-week age, female, SLC, Shizuoka, Japan) were selected and used as experimental animals. Seven healthy SPF Balb/c mice were obtained and refined for 34 days. Then, ten experimental animals which had constant body weights were selected for each group, and the experimental animals were divided into seven groups as illustrated in Table 3 below, and used in the experiment. All experimental animals were fasted for eighteen hours overnight before the start date of administering hG-CSF and the drug and a final autopsy date (drinking water was freely provided), and the objects were identified using picric acid.

TABLE 3

| Group | Inducer | Test substances and dose (mg/kg/day) | Animal No. |
| --- | --- | --- | --- |
| GCSF-2012-PD: Effects on the hG-CSF-treated mice | | | |
| Control | Saline 10 ml/kg | Distilled water oral 10 ml/kg [Intact vehicle] | M01-M10 |
| Control | hG-CSF 250 µg/kg | Distilled water oral 10 ml/kg [hG-CSF] | M11-M20 |
| Active | hG-CSF 250 µg/kg | PMT oral (200 mg/kg) [PMT] | M21-M30 |
| Active | hG-CSF 250 µg/kg | SCGBT oral (200 mg/kg) [SCGBT] | M31-M40 |
| Active | hG-CSF 250 µg/kg | AR oral (200 mg/kg) [AR] | M41-M50 |
| Active | hG-CSF 250 µg/kg | CCP oral (200 mg/kg) [CCP] | M51-M60 |
| Active | hG-CSF 250 µg/kg | AGR oral (200 mg/kg) [AGR] | M61-M70 |

1-3. Administration Method

Administration of hG-CSF and Candidate Drugs

In accordance with previous methods (Verma et al., 1997; Levesque et al., 2003), 250 µg/kg of the hG-CSF (Life Technologies, Carlsbad, Calif., USA) was subcutaneously administered once per day for six consecutive days to promote proliferation of leukocytes and mobilization of bone marrow derived stem cells, and within five minutes of administering the hG-CSF, 200 mg/kg of PMT, SCGBT, astragali radix, cervi cornu parvum, and angelicae gigantis radix extracts were orally administered once per day for the six consecutive days. All five types of natural product derived extracts were dissolved in sterilized distilled water and forcibly orally administered in a volume of 10 mL per kg of animal body weight using a 1 mL syringe to which a metallic zonde was attached, and the hG-CSF was dissolved in normal saline and subcutaneously administered in a volume of 10 ml/kg in dorsal subcutaneous portions. Only sterilized distilled water of the same volume was administered in an hG-CSF control group instead of the natural product derived extracts, and normal saline and sterilized distilled water of the same volume were administered at five minute intervals in a normal media control group instead of the hG-CSF and the natural product derived extracts. The administration amount of the natural product derived extracts used in the present experiment, i.e., 200 mg/kg, was selected based on results of individual animal experiments.

1-4. Observations

Together with changes in body weights and spleen weights, and total number of bone marrow nuclear cells and blood leukocytes, numbers of CD34+ and CD45+ cells, which are representative markers of bone marrow derived stem cells, were observed in bone marrow and blood by a method of using the fluorescence activated cell sorter (FACs). In addition, the numbers of CD34+ and CD45+ cells per unit area in tissue samples of spleens and bone marrow were observed using an area histochemical method, and total thicknesses of spleens, amounts and diameters of white pulp, and amounts of red pulp in spleens and nuclear cells in bone marrow per unit area were also evaluated using an automatic image analyzer (iSolution FL ver 9.1, IMT i-solution Inc., Quebec, Canada). To observe clearer changes, a % change between the normal media control group and the hG-CSF control group, and % changes between each of the groups to which natural product derived extracts were administered and the hG-CSF control group were calculated and compared.

Example 2. Confirmation of Changes in Weights and Weight Gains

Figure 2:
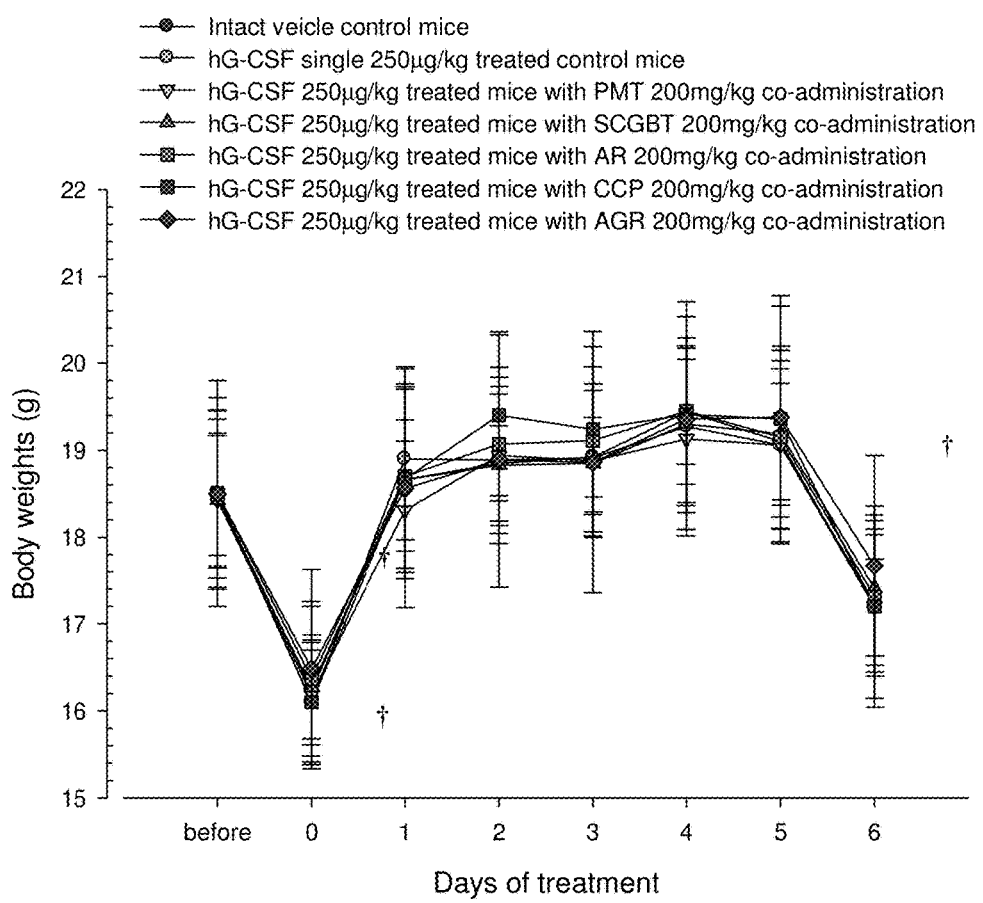
FIG. 2 is a view illustrating results of changes in body weights and body weight gain of mice due to administration of the hG-CSF or a natural product derived candidate substance.

As a result of the observation, changes in weights and weight gains were measured and are illustrated in Table 4 and FIG. 2. As can be seen in FIG. 2, compared with the normal media control group, significant changes in weights and weight gains related to administration of the hG-CSF or the natural product derived candidate substances were not seen in the entire period of the experiment.

TABLE 4

| Groups | Body weight(g) | | Body weight gains (g) during treatment [B − A] |
|---|---|---|---|
| | At first treatment [A] | Sacrifice [B] | |
| Controls | | | |
| Intact vehicle | 16.24 ± 0.63 | 17.19 ± 0.56 | 0.95 ± 0.44 |
| hG-CSF | 16.10 ± 0.68 | 17.24 ± 0.79 | 1.14 ± 0.36 |
| Natural extract orally co-administered | | | |
| PMT | 16.19 ± 0.51 | 17.20 ± 1.06 | 1.01 ± 0.76 |
| SCGBT | 16.27 ± 0.93 | 17.41 ± 0.78 | 1.14 ± 0.55 |
| AR | 16.37 ± 0.89 | 17.31 ± 0.79 | 0.94 ± 0.51 |
| CCP | 16.10 ± 0.71 | 17.20 ± 1.16 | 1.10 ± 0.51 |
| AGR | 16.48 ± 1.15 | 17.67 ± 1.27 | 1.19 ± 0.57 |

Values are expressed mean±S.D. of 10 mice

However, the hG-CSF control group exhibited a 20.00% change in the weight gain amount compared to the normal media control group during the six days of the entire experiment period, and the groups to which 200 mg/kg of PMT, SCGBT, astragali radix, cervi cornu parvum, and angelicae gigantis radix extracts were administered exhibited changes of −11.40, 0.00, −17.54, −3.51, and 4.39%, respectively, compared to the hG-CSF control group.

Example 3. Confirmation of Changes in Weights of Spleens

Amounts of changes in the weights of spleens observed in the present example are illustrated in Table 5 below. Significant ($p<0.01$) increase in relative weights with respect to spleens and body weights due to noticeable splenomegaly was seen in the hG-CSF control group compared to the normal media control group, and significant ($p<0.01$) decrease in weights of spleens were seen in the groups to which PMT and angelicae gigantis radix extracts were administered compared to the hG-CSF control group.

TABLE 5

| | Spleen weights | |
|---|---|---|
| Groups | Absolute (g) | Relative (% of body weight) |
| Controls | | |
| Intact vehicle | 0.066 ± 0.005 | 0.384 ± 0.018 |
| hG-CSF | 0.132 ± 0.012* | 0.768 ± 0.090* |
| Natural extract orally co-administered | | |
| PMT | 0.104 ± 0.008$^{ab}$ | 0.608 ± 0.064$^{ab}$ |
| SCGBT | 0.139 ± 0.019$^{a}$ | 0.803 ± 0.128$^{a}$ |
| AR | 0.125 ± 0.011$^{a}$ | 0.721 ± 0.050$^{a}$ |
| CCP | 0.150 ± 0.018$^{ac}$ | 0.871 ± 0.085$^{ac}$ |
| AGR | 0.109 ± 0.008$^{ab}$ | 0.618 ± 0.061$^{ab}$ |

Figure 3:
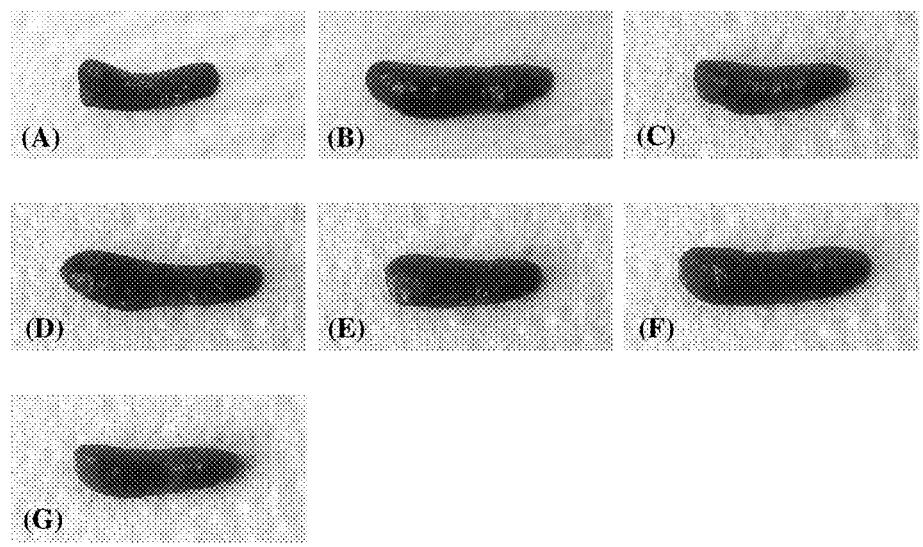
FIG. 3 is a view illustrating results of checking sizes of spleens of the mice to which the hG-CSF or the natural product derived candidate substance was administered (A: untreated, B: hG-CSF, C: palmultang+hG-CSF, D: samchulgeonbitang+hG-CSF, E: astragali radix+hG-CSF, F: cervi cornu parvum+hG-CSF, and G: angelicae gigantis radix+hG-CSF).
Figure 4A:
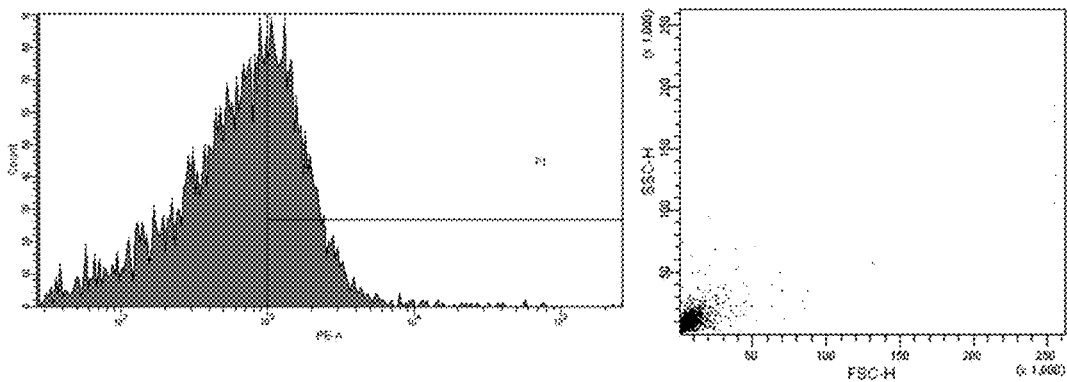
FIGS. 4 and 5 are views illustrating results of observing a fluorescence-activated cell sorter (FACS) of CD34+ cells of the mice to which the hG-CSF or the natural product derived candidate substance was administered (A: untreated, B: hG-CSF, C: palmultang+hG-CSF, D: samchulgeonbitang+hG-CSF, E: astragali radix+hG-CSF, F: cervi cornu parvum+hG-CSF, and G: angelicae gigantis radix+hG-CSF).
Figure 4B:
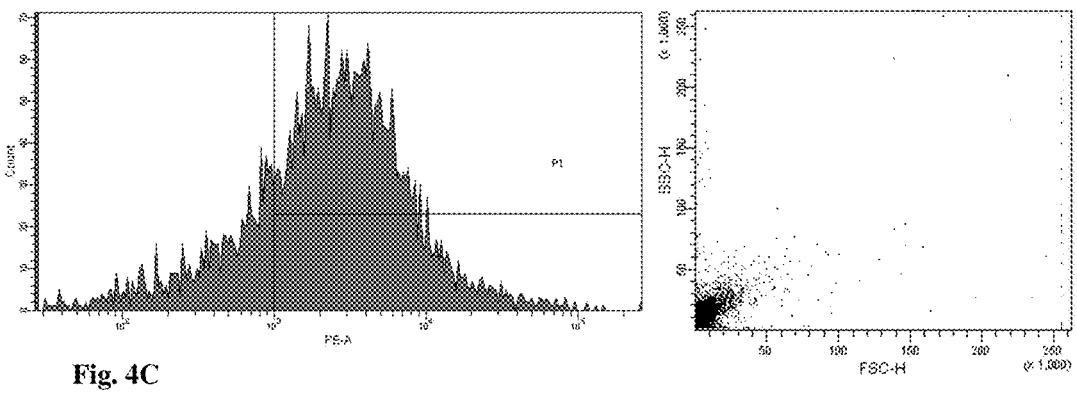
Figure 4C:
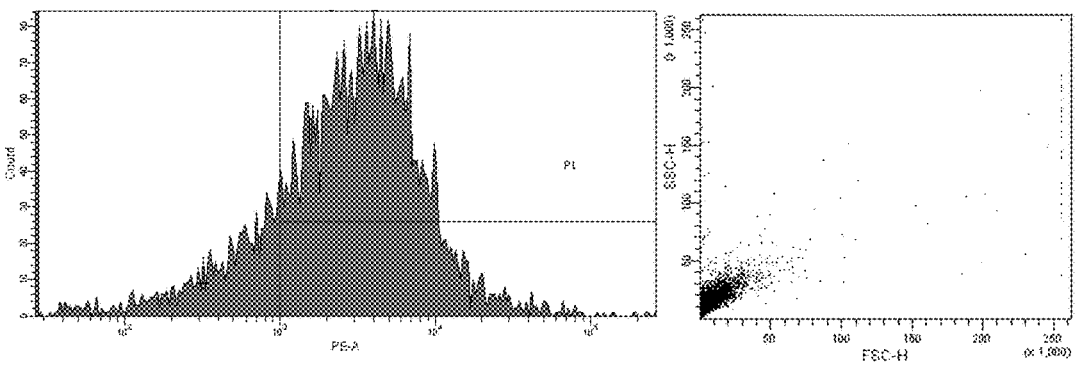
Figure 4D:
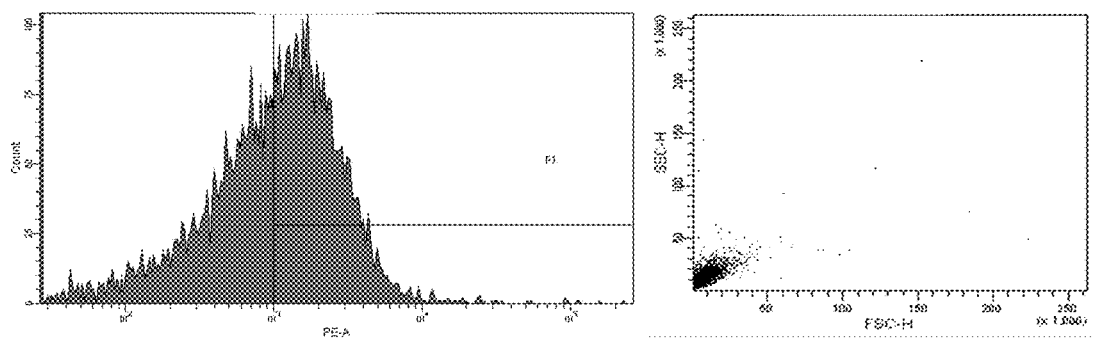
Figure 4E:
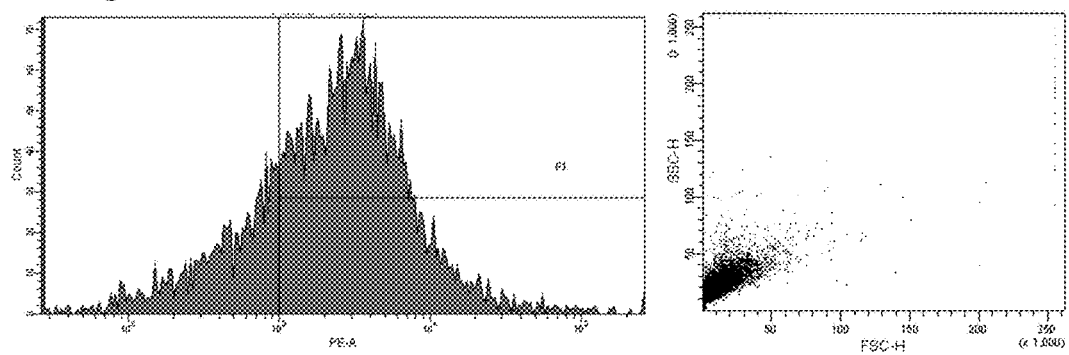
Figure 4F:
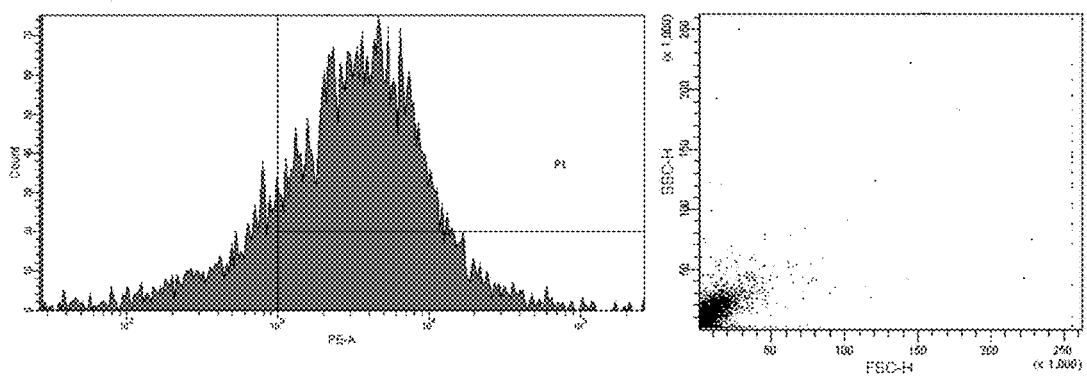
Figure 4G:
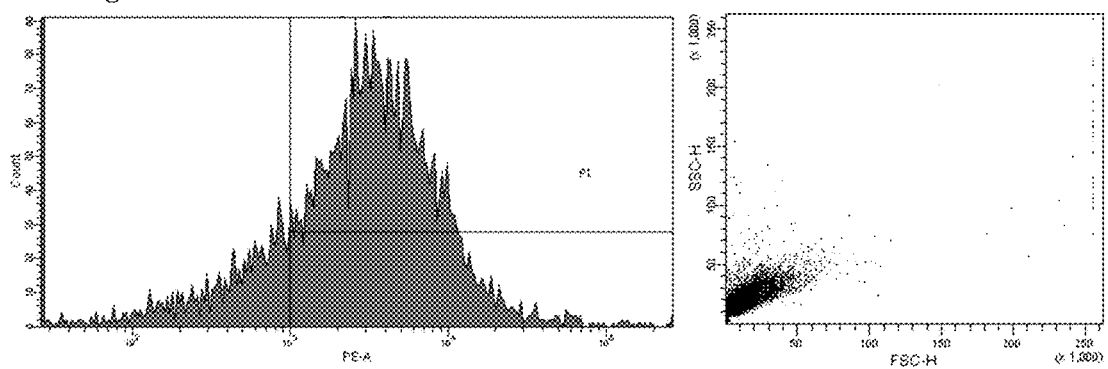
Figure 5A:
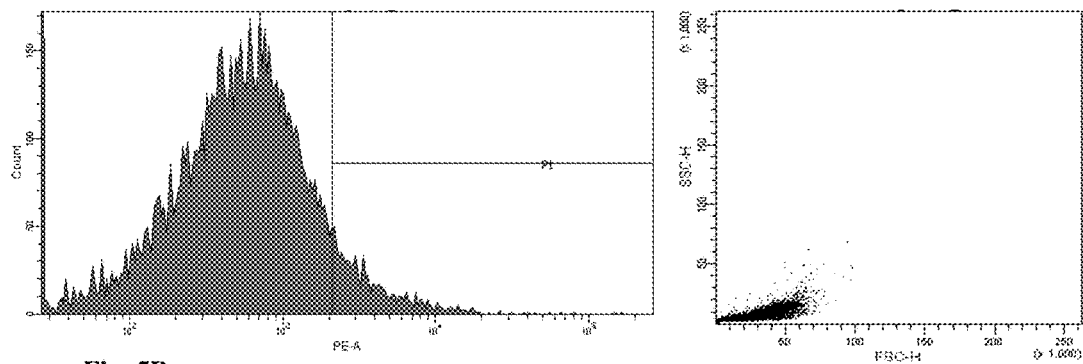
Figure 5B:
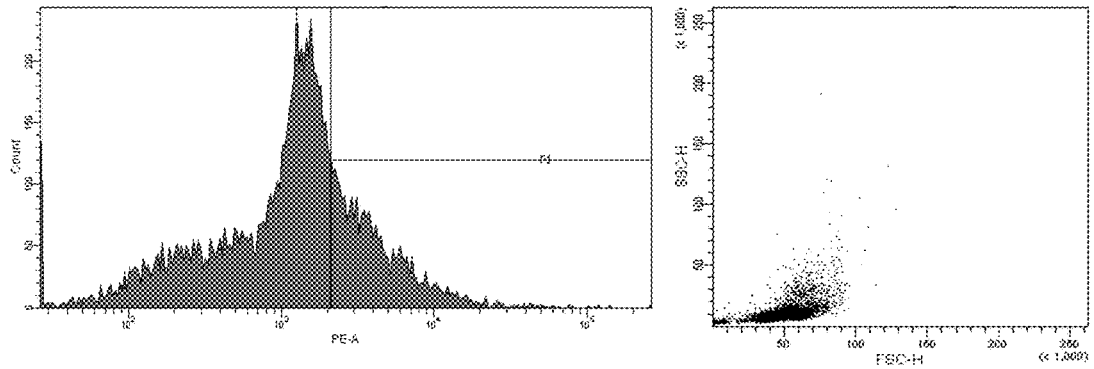
Figure 5C:
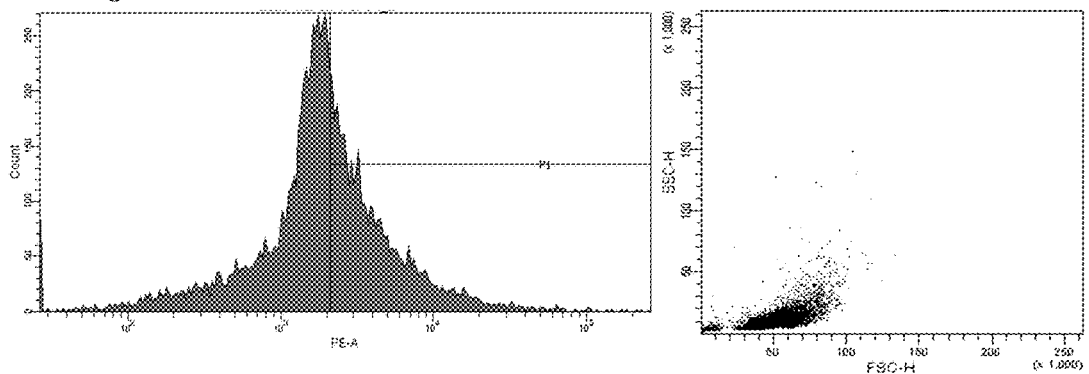
Figure 5D:
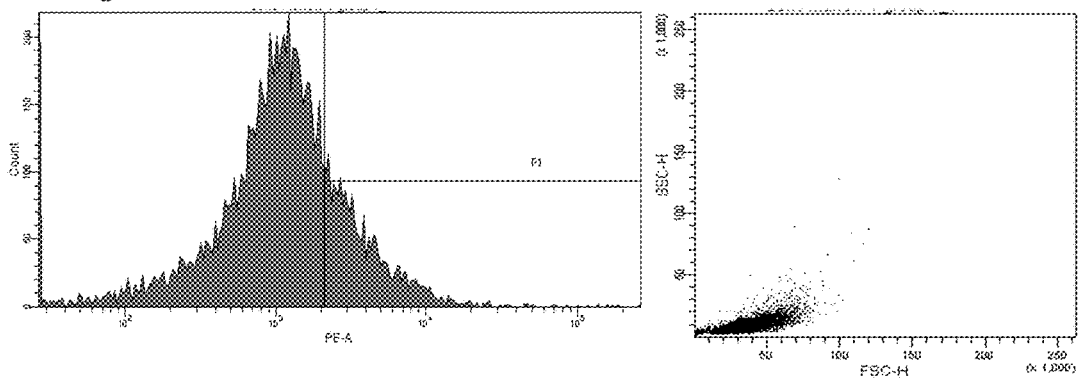
Figure 5E:
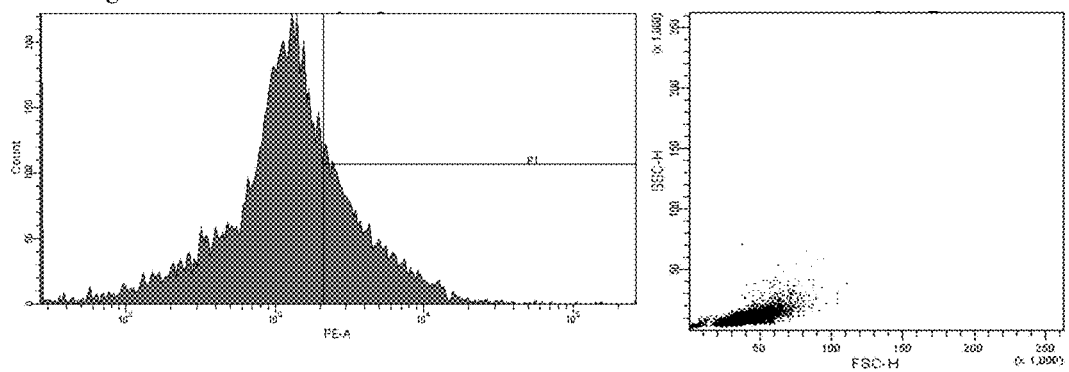
Figure 5F:
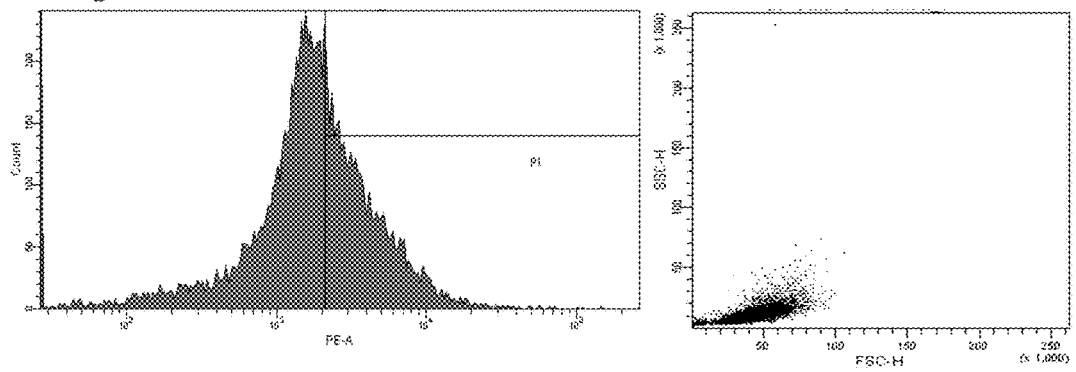
Figure 5G:
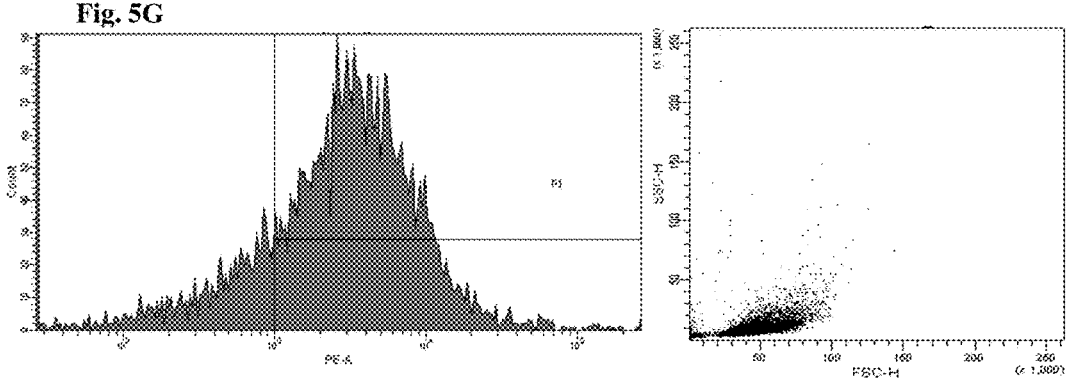
Figure 6A:
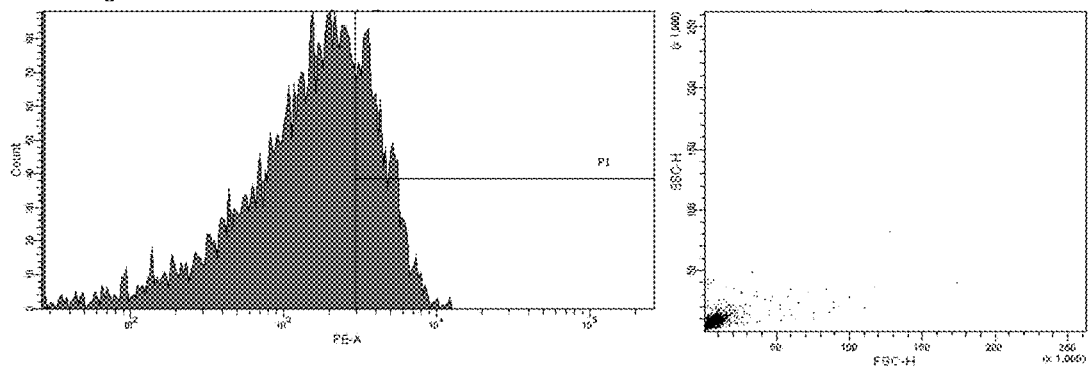
FIGS. 6 and 7 are views illustrating results of observing a FACS of CD45+ cells of the mice to which the hG-CSF or the natural product derived candidate substance was administered (A: untreated, B: hG-CSF, C: palmultang+hG-CSF, D: samchulgeonbitang+hG-CSF, E: astragali radix+hG-CSF, F: cervi cornu parvum+hG-CSF, and G: angelicae gigantis radix+hG-CSF).
Figure 6B:
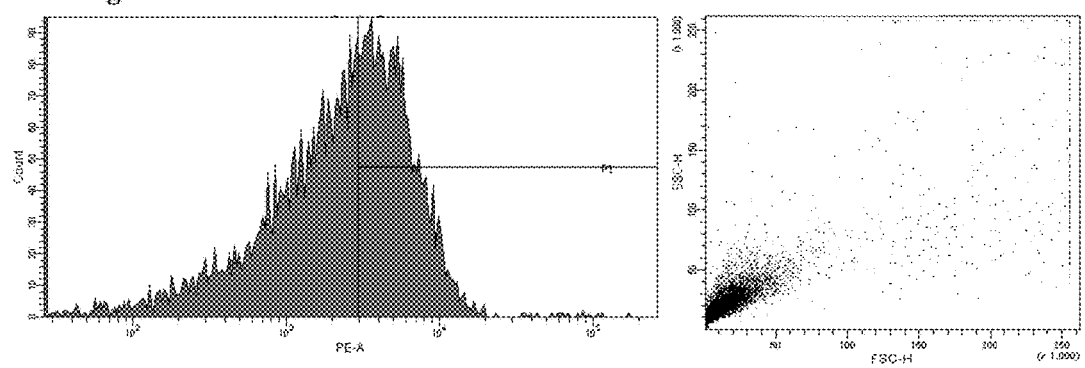
Figure 6C:
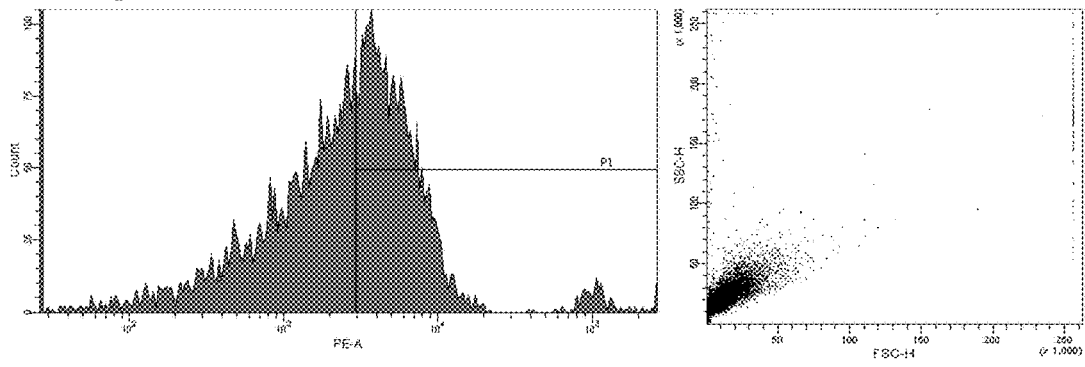
Figure 6D:
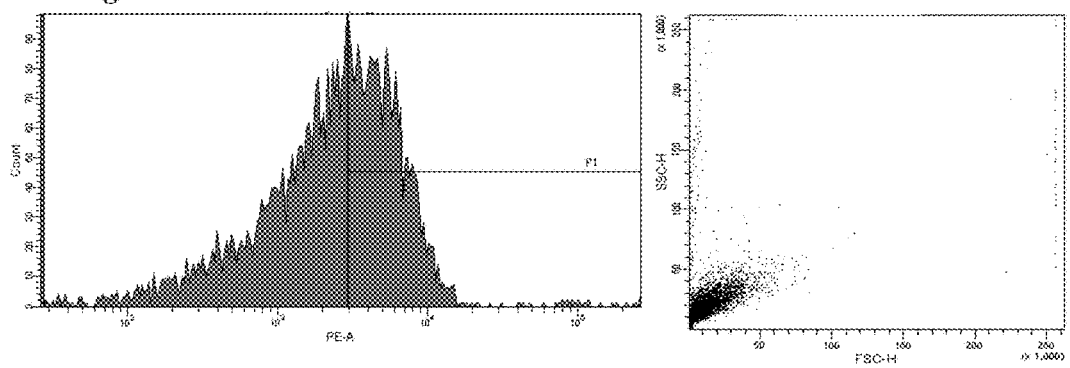
Figure 6E:
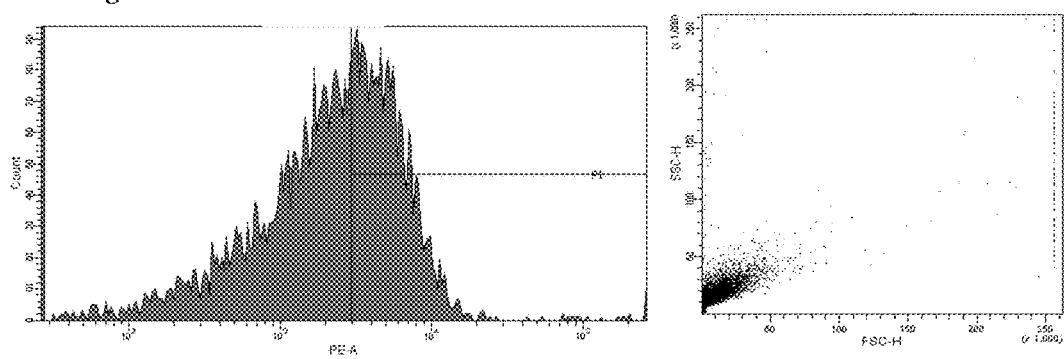
Figure 6F:
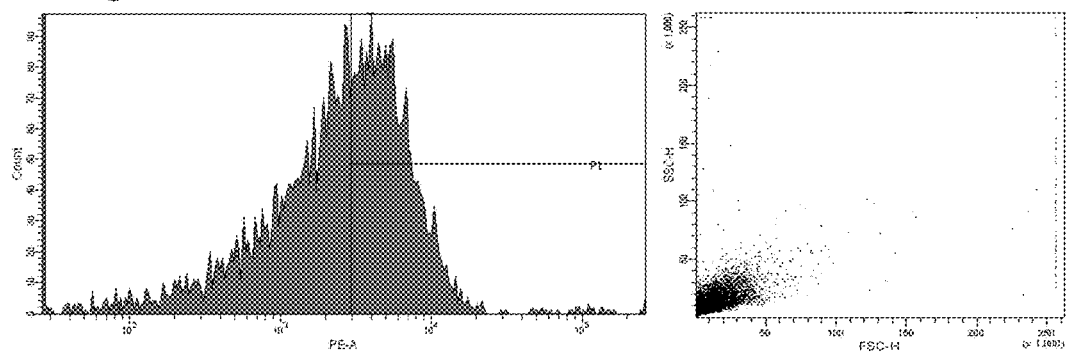
Figure 6G:
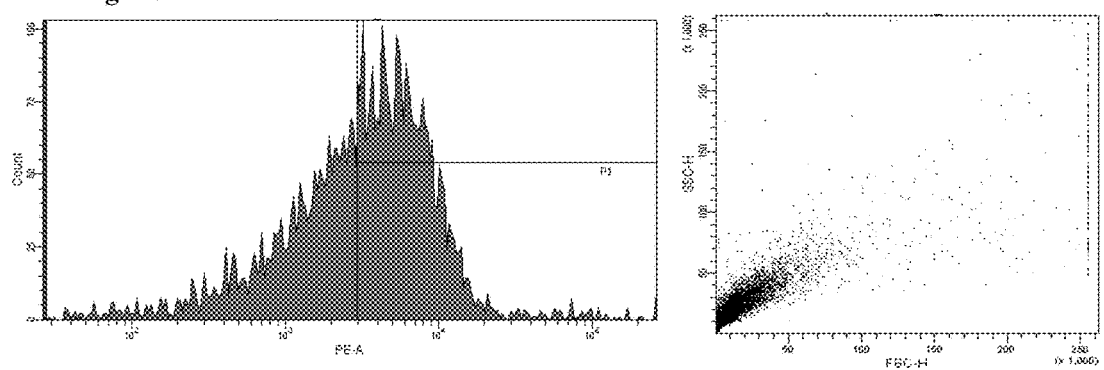
Figure 7A:
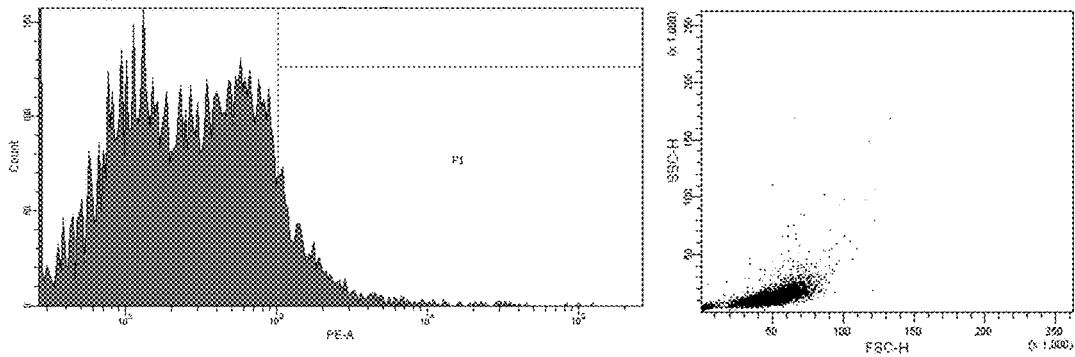
Figure 7B:
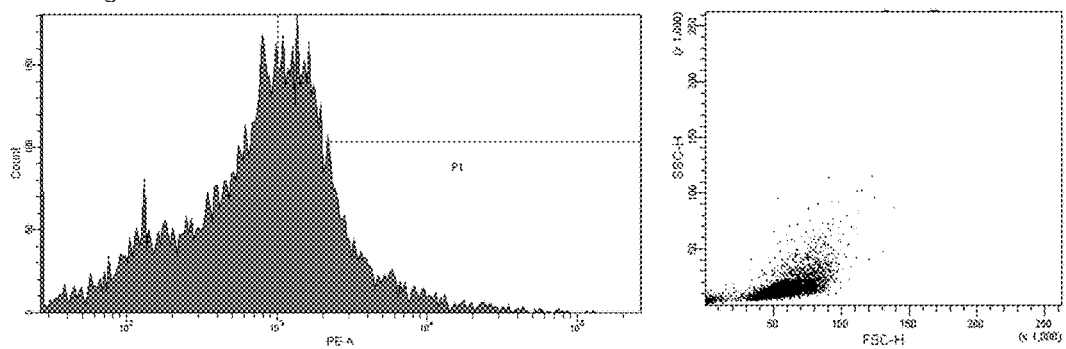
Figure 7C:
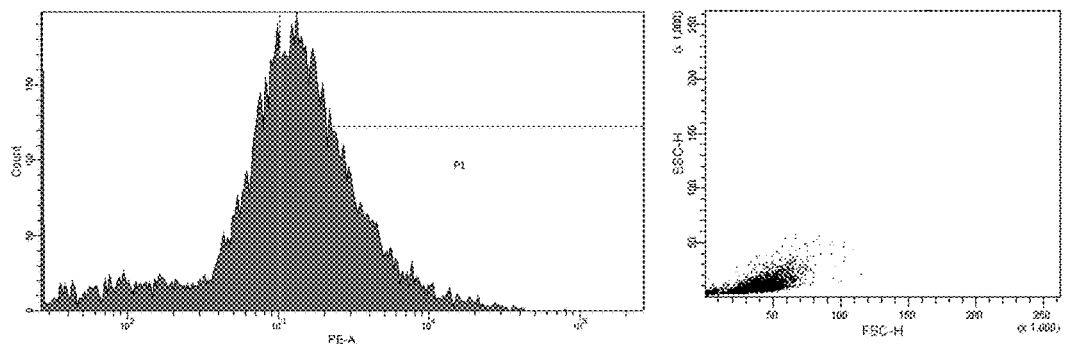
Figure 7D:
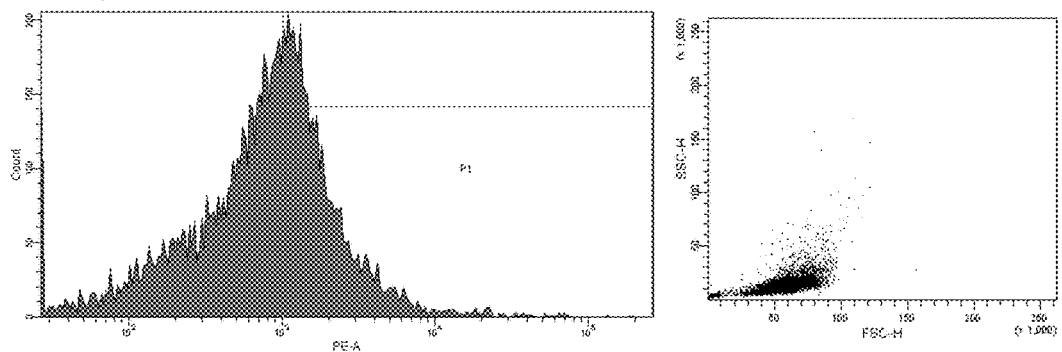
Figure 7E:
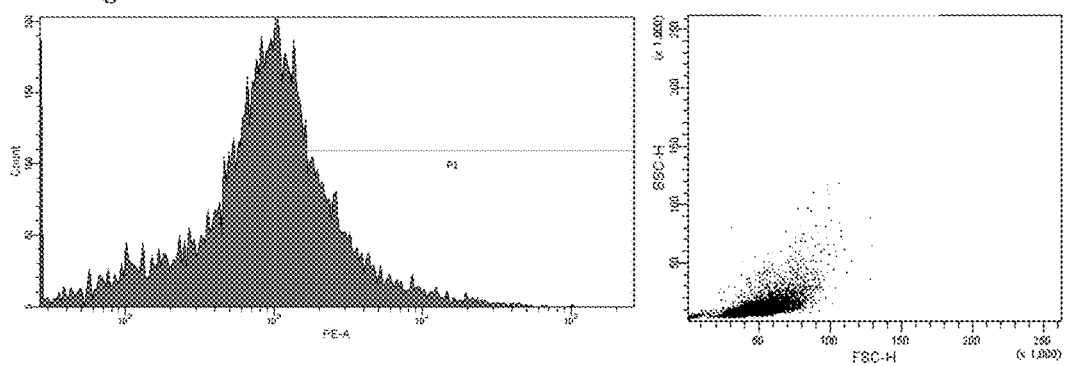
Figure 7F:
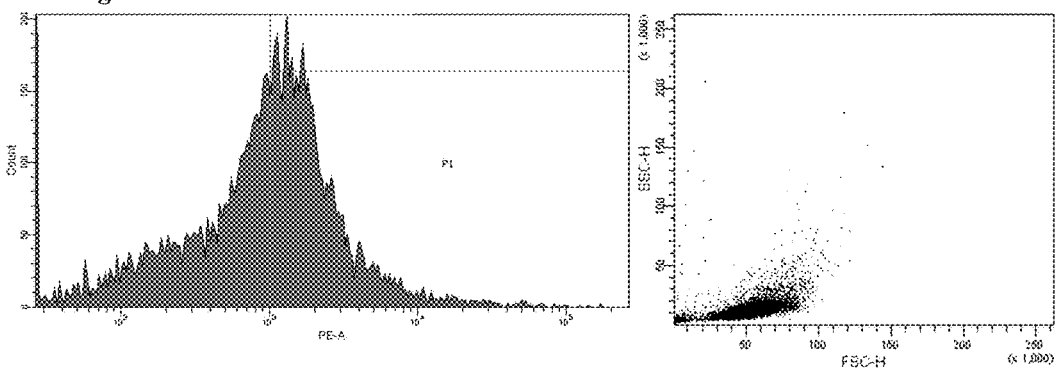
Figure 7G:
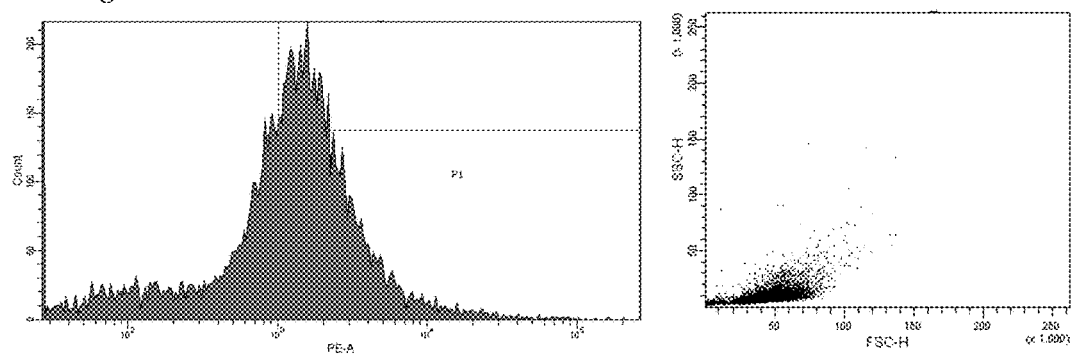

In addition, as illustrated in FIG. 3, as a result of checking the sizes of the spleens with the naked eye, it was confirmed that the sizes of spleens of the groups to which PMT and angelicae gigantis radix extracts were administered decreased compared to the normal media control group.

Meanwhile, significant ($p<0.05$) increase in absolute and relative weights of spleens was seen in the cervi cornu parvum administration group compared to the hG-CSF control group, and significant changes in the weights of the spleens were not seen in the groups to which SCGBT and astragali radix extracts were administered compared to the hG-CSF control group.

The hG-CSF control group exhibited a 99.55% change in the absolute weights of spleens compared to the normal media control group, and the groups to which 200 mg/kg of PMT, SCGBT, astragali radix, cervi cornu parvum, and angelicae gigantis radix extracts were administered exhibited changes of −21.08, 5.61, −5.38, 13.65, and −17.51%, respectively, compared to the hG-CSF control group.

The hG-CSF control group exhibited a 99.81% change in the relative weights of spleens compared to the normal media control group, and the groups to which 200 mg/kg of PMT, SCGBT, astragali radix, cervi cornu parvum, and angelicae gigantis radix extracts were administered exhibited changes of −20.85, 4.57, −6.13, 13.46, and −19.46%, respectively, compared to the hG-CSF control group.

From the above results, it was confirmed that co-administration of the G-CSF and the angelicae gigantis radix extract can mitigate splenomegaly, which is a side effect of the G-CSF.

Example 4. Numerical Confirmation of Blood Leukocytes and Nuclear Cells in Bone Marrow In the present experiment, numerical changes in blood leukocytes and bone marrow nuclear cells were observed and the results thereof are illustrated in Table 6.

TABLE 6

| Groups | Total Cell Counts | |
|---|---|---|
| | Blood leukocytes ($\times 10^3$ cells/μl) | Bone marrow nuclear cells ($\times 10^4$ cells/μl) |
| Controls | | |
| Intact vehicle | 5.06 ± 2.00 | 47.10 ± 20.93 |
| hG-CSF | 53.40 ± 22.63$^a$ | 457.90 ± 129.50$^c$ |
| Natural extract orally co-administered | | |
| PMT | 55.50 ± 17.92$^a$ | 440.80 ± 115.78$^c$ |
| SCGBT | 47.70 ± 13.34$^a$ | 444.10 ± 105.38$^c$ |
| AR | 52.50 ± 11.74$^a$ | 431.90 ± 127.46$^c$ |
| CCP | 73.00 ± 12.94$^{ab}$ | 590.10 ± 134.67$^c$ |
| AGR | 57.10 ± 16.93$^a$ | 444.80 ± 92.76$^c$ |

Although significant (p<0.01) increases in total numbers of blood leukocytes and bone marrow nuclear cells were seen in the hG-CSF control group compared to the normal media control group, significant changes in the total numbers of blood leukocytes and bone marrow nuclear cells were not seen in any of the natural product extract co-administration groups except that noticeable increases in the total numbers of blood leukocytes and bone marrow nuclear cells were seen in the cervi cornu parvum co-administration group.

The hG-CSF control group exhibited a 955.34% change in the total number of blood leukocytes compared to the normal media control group, and the groups to which 200 mg/kg of PMT, SCGBT, astragali radix, cervi cornu parvum, and angelicae gigantis radix extracts were administered exhibited changes of 3.93, −10.67, −1.69, 36.70, and 6.93%, respectively, compared to the hG-CSF control group.

The hG-CSF control group exhibited a 872.19% change in the total number of bone marrow nuclear cells compared to the normal media control group, and the groups to which 200 mg/kg of PMT, SCGBT, astragali radix, cervi cornu parvum, and angelicae gigantis radix extracts were administered exhibited changes of −3.73, −3.01, −5.68, 28.87, and −2.86%, respectively, compared to the hG-CSF control group.

Consequently, it was confirmed that the total numbers of blood leukocytes and bone marrow nuclear cells were not increased compared to the hG-CSF control group when the angelicae gigantis radix extract was administered, but remained at a similar increasing level.

Example 5. Results of FACs: Confirmation of Numerical Changes in CD34+ and CD45+ Cells in Blood and Bone Marrow Numerical changes in CD34+ and CD45+ cells in blood and bone marrow were observed by a method using the FACs, and the results thereof are illustrated in Table 7.

TABLE 7

| Groups | Blood leukocytes | | Bone marrow nuclear cells | |
|---|---|---|---|---|
| | CD34+ cells ($\times 10^2$ cells/μl) | CD45+ cells ($\times 10^2$ cells/μl) | CD34+ cells ($\times 10^2$ cells/μl) | CD45+ cells ($\times 10^2$ cells/μl) |
| Controls | | | | |
| Intact vehicle | 7.93 ± 1.05 | 10.41 ± 1.47 | 16.60 ± 3.76 | 13.16 ± 2.32 |
| hG-CSF | 26.81 ± 6.02$^a$ | 42.94 ± 8.62$^a$ | 30.41 ± 6.69$^a$ | 24.63 ± 3.82$^a$ |
| Natural extract orally co-administered | | | | |
| PMT | 43.40 ± 5.46$^a$ | 61.99 ± 3.32$^{ab}$ | 45.09 ± 5.83$^{ab}$ | 32.35 ± 1.77$^{ab}$ |
| SCGBT | 22.14 ± 5.46$^a$ | 41.76 ± 6.09$^a$ | 31.21 ± 1.60$^a$ | 25.37 ± 2.47$^a$ |
| AR | 25.10 ± 6.36$^a$ | 45.78 ± 8.58$^a$ | 32.42 ± 3.31$^a$ | 23.97 ± 2.46$^a$ |
| CCP | 40.66 ± 2.59$^{ab}$ | 56.79 ± 6.14$^{ab}$ | 40.44 ± 1.13$^{ab}$ | 28.44 ± 4.73$^a$ |
| AGR | 41.25 ± 6.00$^a$ | 61.28 ± 7.68$^{ab}$ | 44.34 ± 3.59$^{ab}$ | 31.17 ± 2.59$^{ab}$ |

Values are expressed mean±S.D. of 5 mice 5.1. Numerical Changes in CD34+ Cells in Blood and Bone Marrow FACS observation results of CD34+ cells are illustrated in FIGS. 4 and 5. When the results are viewed in conjunction with Table 7, significant (p<0.01) numerical increase in CD34+ cells in blood and bone marrow was seen in the hG-CSF control group compared to the normal media control group, and significant (p<0.01) numerical increases in CD34+ cells in blood and bone marrow were seen in the groups to which PMT, cervi cornu parvum, and angelicae gigantis radix extracts were administered even when compared to the hG-CSF control group. Meanwhile, significant numerical increases in CD34+ cells in blood and bone marrow were not seen in the groups to which SCGBT and astragali radix extracts were administered compared to the hG-CSF control group.

The hG-CSF control group exhibited a 238.08% change in the number of CD34+ cells in blood compared to the normal media control group, and the groups to which 200 mg/kg of PMT, SCGBT, astragali radix, cervi cornu parvum, and angelicae gigantis radix extracts were administered exhibited changes of 61.89, −17.41, −6.39, 51.65, and 53.85%, respectively, compared to the hG-CSF control group.

The hG-CSF control group exhibited a 83.14% change in the number of CD34+ cells in bone marrow compared to the normal media control group, and the groups to which 200 mg/kg of PMT, SCGBT, astragali radix, cervi cornu parvum, and angelicae gigantis radix extracts were administered exhibited changes of 48.29, 2.64, 6.62, 33.00, and 45.80%, respectively, compared to the hG-CSF control group.

By the above results, compared with a case only G-CSF is administered, it was confirmed that the numbers of CD34+ cells in the blood and the bone marrow significantly increase when the angelicae gigantis radix extract is co-administered with the G-CSF.

5.2. Numerical Changes in CD45+ Cells in Blood and Bone Marrow

FACs observation results of CD45+ cells are illustrated in FIGS. 6 and 7. When the results are viewed in conjunction with Table 7, significant (p<0.01) numerical increase in CD45+ cells in blood and bone marrow was seen in the hG-CSF control group compared to the normal media control group, and significant (p<0.01) numerical increases in CD45+ cells in blood and bone marrow were seen in the groups to which PMT, cervi cornu parvum, and angelicae gigantis radix extracts were administered even when compared to the hG-CSF control group. Meanwhile, significant numerical increases in CD45+ cells in blood and bone marrow were not seen in the groups to which SCGBT and astragali radix extracts were administered compared to the hG-CSF control group.

The hG-CSF control group exhibited a 312.39% change in the number of CD45+ cells in blood compared to the normal media control group, and the groups to which 200 mg/kg of PMT, SCGBT, astragali radix, cervi cornu parvum, and angelicae gigantis radix extracts were administered exhibited changes of 44.38, −2.75, 5.45, 32.26, and 42.72%, respectively, compared to the hG-CSF control group.

The hG-CSF control group exhibited a 87.18% change in the number of CD45+ cells in bone marrow compared to the normal media control group, and the groups to which 200 mg/kg of PMT, SCGBT, astragali radix, cervi cornu parvum, and angelicae gigantis radix extracts were administered exhibited changes of 31.35, 3.02, −2.68, 15.47, and 26.58%, respectively, compared to the hG-CSF control group.

By comparing the above results with a case in which only G-CSF is administered, it was confirmed that the numbers of CD45+ cells in the blood and the bone marrow significantly increase when the angelicae gigantis radix extract is co-administered with the G-CSF.

Consequently, referring to the results of examples 5.1 and 5.2, it can be confirmed that the co-administration of the angelicae gigantis radix extract significantly increases proliferation of the bone marrow derived stem cells.

Example 6. Confirmation of Histopathological Changes

Histopathological changes of spleens and femoral bone marrow were observed in eight groups and values thereof are illustrated in Table 8 below.

Values are expressed mean±S.D. of 10 mice 6.1. Histopathological Change in Spleens As can be seen in Table 8 above, the hG-CSF control group showed a feature of splenomegaly caused by significant infiltration of nuclear cells in red pulp of spleens. Although significant (p<0.01) increases in the total thicknesses of the spleens and nuclear cells per unit area of the red pulp were seen compared to the normal media control group, the amount and the diameter of white pulp was observed to be similar with the normal media control group.

Figure 8:
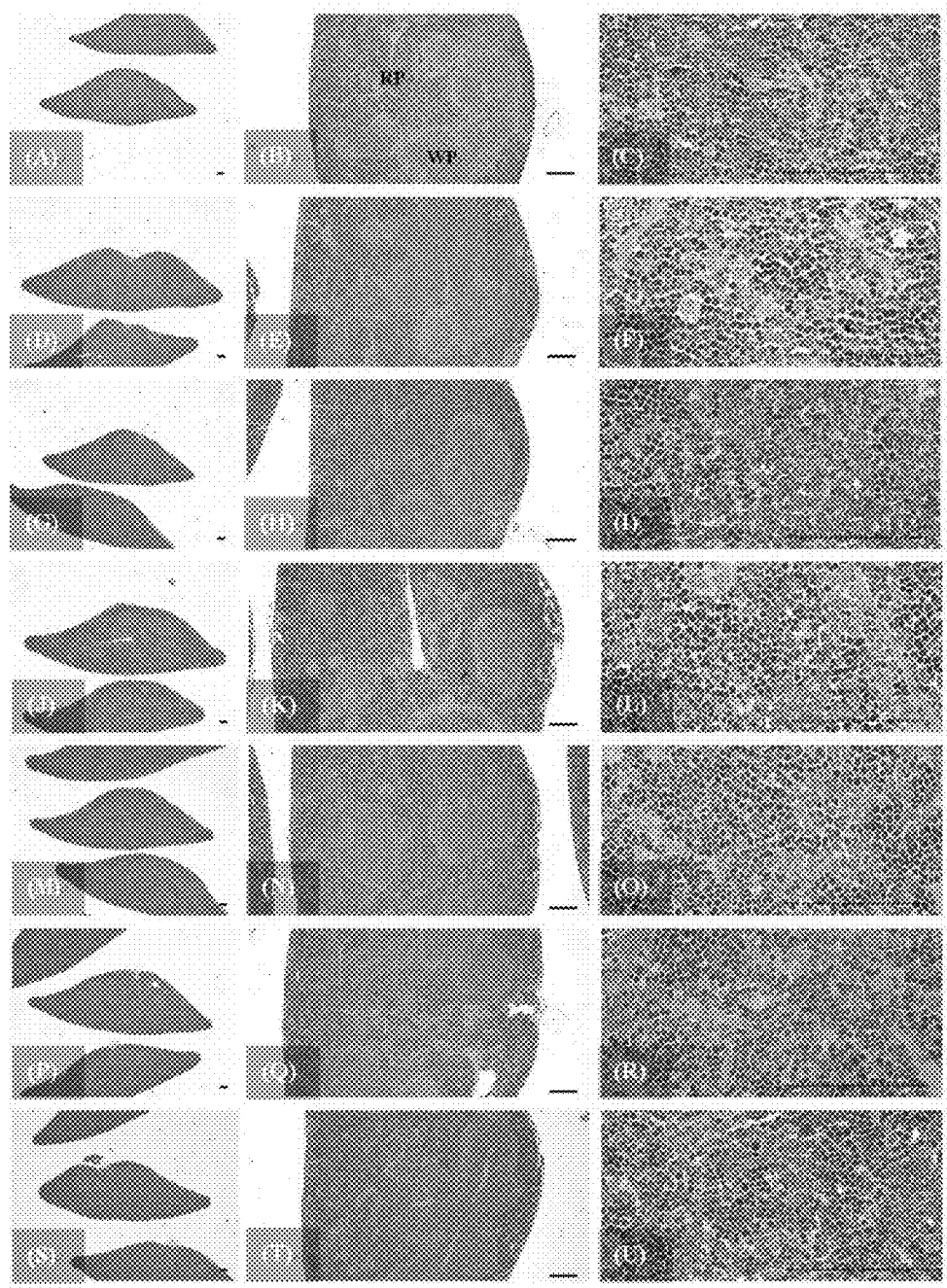
FIG. 8 is a view illustrating observations of total thicknesses of spleens and nuclear cells per unit area of red pulp and white pulp of the spleens of the mice to which the hG-CSF or the natural product derived candidate substance was administered (A-C: untreated, D-F: hG-CSF, G-I: palmultang+hG-CSF, J-L: samchulgeonbitang+hG-CSF, M-O: astragali radix+hG-CSF, P-R: cervi cornu parvum+hG-CSF, and S-U: angelicae gigantis radix+hG-CSF).

FIG. 8 is a picture illustrating total thicknesses of the spleens and the numbers of nuclear cells per unit area of the red pulp and the white pulp of the spleens. As can be seen in FIG. 8, although the groups to which PMT and angelicae gigantis radix extracts were administered showed significant (p<0.01) decreases in the total thicknesses of the spleens and the numbers of nuclear cells per unit area of the red pulp of the spleens compared to the hG-CSF control group, the SCGBT administration group showed a significant (p<0.01) increase in the total thickness of the spleen compared to the hG-CSF control group, and the groups to which the astragali radix and cervi cornu parvum extracts were administered showed no significant histopathological changes in the spleens compared to the hG-CSF control group.

The hG-CSF control group exhibited a 17.47% change in the total thickness of the spleen compared to the normal media control group, and the groups to which 200 mg/kg of PMT, SCGBT, astragali radix, cervi cornu parvum, and angelicae gigantis radix extracts were administered exhibited changes of −12.02, 10.72, −0.48, 7.81, and −9.75%, respectively, compared to the hG-CSF control group.

The hG-CSF control group exhibited a 0.69% change in the amount of white pulp in the spleen compared to the normal media control group, and the groups to which 200 mg/kg of PMT, SCGBT, astragali radix, cervi cornu parvum, and angelicae gigantis radix extracts were administered exhibited changes of −3.42, −4.11, 1.37, 2.05, and 0.00%, respectively, compared to the hG-CSF control group.

The hG-CSF control group exhibited a 4.17% change in the mean diameter of the white pulp of the spleen compared to the normal media control group, and the groups to which 200 mg/kg of PMT, SCGBT, astragali radix, cervi cornu parvum, and angelicae gigantis radix extracts were administered exhibited changes of 3.09, 1.34, 0.77, 1.96, and −1.26%, respectively, compared to the hG-CSF control group.

TABLE 8

| Groups | Spleen | | | | Bone marrow Mean number of nuclear cells (×$10^2$ cells/mm$^2$) |
| | Total thickness (mm/central regions) | Number of white pulp (white pulps/mm$^2$) | Mean diameters of white pulp (μm/white pulp) | Mean number of red pulp nuclear cells (×$10^2$ cells/mm2) | |
| --- | --- | --- | --- | --- | --- |
| Controls | | | | | |
| Intact vehicle | 1.58 ± 1.16 | 14.50 ± 2.37 | 459.22 ± 98.51 | 3.34 ± 0.80 | 16.30 ± 2.26 |
| hG-CSF | 1.86 ± 0.12a | 14.60 ± 1.84 | 478.38 ± 70.00 | 27.18 ± 5.19a | 74.51 ± 18.28a |
| Natural extract orally co-administered | | | | | |
| PMT | 1.63 ± 0.07b | 14.10 ± 2.33 | 493.19 ± 68.93 | 19.09 ± 2.44ab | 72.46 ± 11.54a |
| SCGBT | 2.06 ± 0.16ab | 14.00 ± 2.98 | 484.79 ± 84.57 | 28.92 ± 5.91a | 70.77 ± 11.22a |
| AR | 1.85 ± 0.18a | 14.80 ± 1.75 | 482.04 ± 116.86 | 30.65 ± 6.14a | 67.22 ± 10.57a |
| CCP | 2.00 ± 0.34a | 14.90 ± 2.60 | 487.78 ± 65.78 | 26.76 ± 3.43a | 80.03 ± 12.18a |
| AGR | 1.68 ± 0.14b | 14.60 ± 2.01 | 472.34 ± 65.60 | 17.61 ± 3.18ab | 67.30 ± 11.77a |

The hG-CSF control group exhibited a 714.75% change in the number of nuclear cells per unit area of the red pulp of the spleen compared to the normal media control group, and the groups to which 200 mg/kg of PMT, SCGBT, astragali radix, cervi cornu parvum, and angelicae gigantis radix extracts were administered exhibited changes of −29.76, 6.39, 12.76, −1.55, and −35.21%, respectively, compared to the hG-CSF control group.

6.2. Histopathological Change in Femoral Bone Marrow

Figure 9:
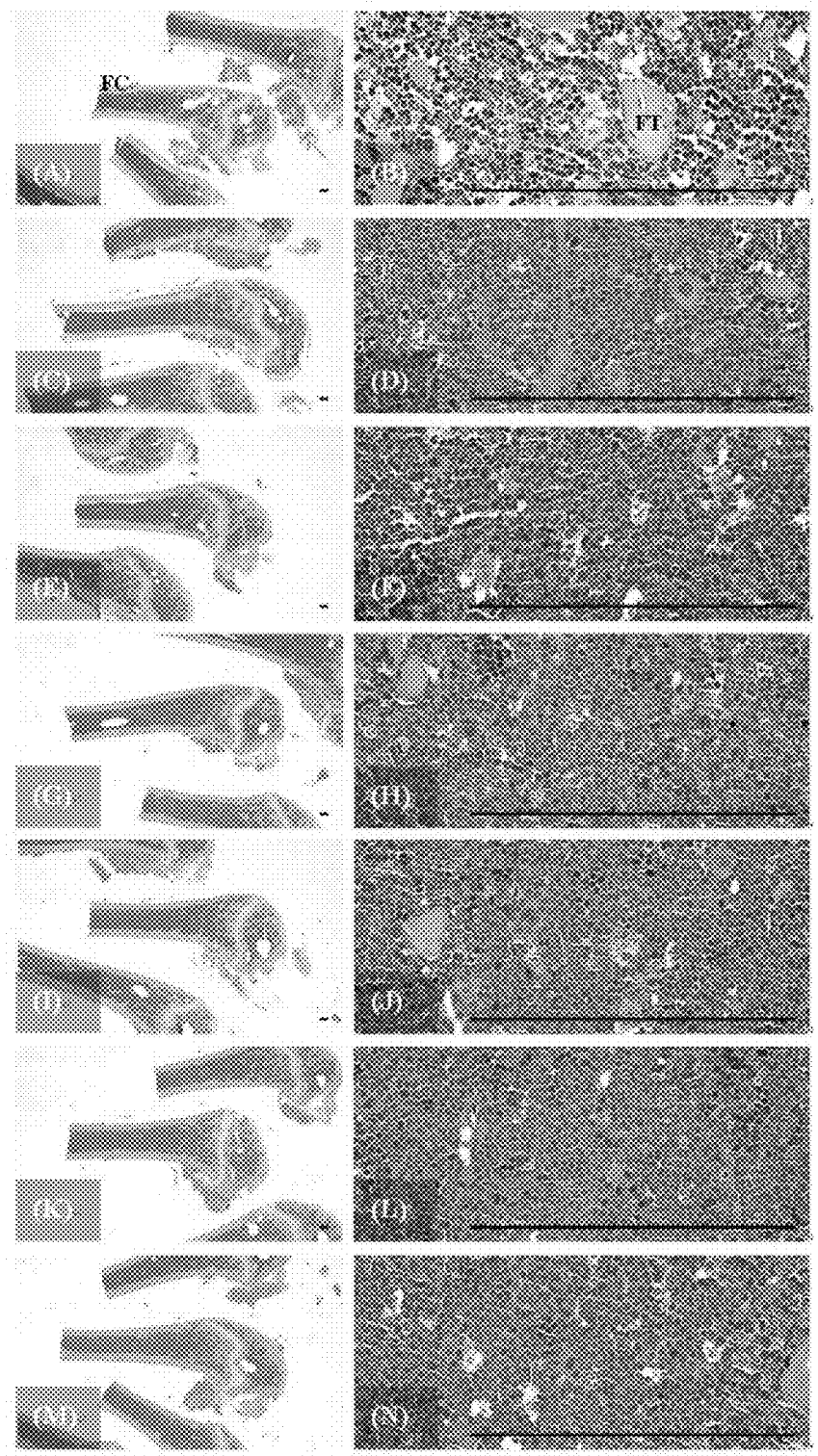
FIG. 9 is a view illustrating observations of a numerical increase in CD34 immunoreactive cells in spleens and bone marrow of the mice to which the hG-CSF or the natural product derived candidate substance was administered (A-B: untreated, C-D: hG-CSF, E-F: palmultang+hG-CSF, G-H: samchulgeonbitang+hG-CSF, I-J: astragali radix+hG-CSF, K-L: cervi cornu parvum+hG-CSF, and M-N: angelicae gigantis radix+hG-CSF).

As can be seen in Table 8 above, the hG-CSF control group showed significant proliferation of granulocytes. As illustrated in FIG. 9, although a significant (p<0.01) increase in nuclear cells per unit area of bone marrow was seen in comparison to the normal media control group, no significant histopathological changes in femoral bone marrow were seen in any of the groups to which natural product derived extracts were administered compared with the hG-CSF control group.

The hG-CSF control group exhibited a 357.02% change in the number of nuclear cells per unit area of the femoral bone marrow compared to the normal media control group, and the groups to which 200 mg/kg of PMT, SCGBT, astragali radix, cervi cornu parvum, and angelicae gigantis radix extracts were administered exhibited changes of −2.75, −5.02, −9.79, 7.40, and −9.68%, respectively, compared to the hG-CSF control group.

From examples 6.1 and 6.2, it can be confirmed that the co-administration of the angelicae gigantis radix can prevent the side effects such as splenomegaly caused by administration of only the G-CSF, and increase leukocytes at the same time.

Example 7. Confirmation of Area Histochemical Change

Numbers of CD34 and CD45 immunoreactive cells in spleens and bone marrow with respect to seven groups are illustrated in Table 9 below.

TABLE 9

| Groups | Spleen immunoreactive cell numbers (cell/mm$^2$) | | Bone marrow immunoreactive cell numbers (cell/mm$^2$) | |
|---|---|---|---|---|
| | CD34+ | CD45+ | CD34+ | CD45+ |
| Controls | | | | |
| Intact vehicle | 16.40 ± 2.72 | 44.90 ± 15.04 | 11.40 ± 3.92 | 35.80 ± 11.86 |
| hG-CSF | 133.40 ± 20.30$^c$ | 303.50 ± 79.69$^c$ | 46.20 ± 9.74$^c$ | 325.40 ± 98.79$^a$ |
| Natural extract orally co-administered | | | | |
| PMT | 174.60 ± 18.35$^{cd}$ | 405.20 ± 64.22$^{cd}$ | 74.20 ± 10.88$^{cd}$ | 490.10 ± 112.39$^{ab}$ |
| SCGBT | 137.70 ± 20.82$^c$ | 300.50 ± 70.36$^c$ | 41.30 ± 6.13$^c$ | 350.00 ± 70.41$^a$ |
| AR | 146.80 ± 14.77$^c$ | 327.50 ± 46.42$^c$ | 49.40 ± 8.83$^c$ | 364.90 ± 116.30$^a$ |
| CCP | 125.50 ± 13.74$^c$ | 478.80 ± 111.65$^{cd}$ | 42.40 ± 6.98$^c$ | 344.40 ± 102.18$^a$ |
| AGR | 160.60 ± 14.21$^{cd}$ | 462.40 ± 80.42$^{cd}$ | 81.00 ± 19.10$^{cd}$ | 536.70 ± 82.72$^{ab}$ |

Values are expressed mean±S.D. of 10 mice 7.1. Numerical Changes in CD34 Immunoreactive Cells in Spleens and Bone Marrow As can be seen in Table 9 and FIG. 9, the hG-CSF control group showed a significant (p<0.01) numerical increase in CD34 immunoreactive cells in spleens and bone marrow compared to the normal media control group, and the groups to which PMT and angelicae gigantis radix extracts were administered showed significant (p<0.01) numerical increases in CD34 immunoreactive cells in the spleens and the bone marrow even when compared to the hG-CSF control group. Meanwhile, no significant numerical changes in CD34 immunoreactive cells per unit area of the spleens and the bone marrow were seen in the groups to which SCGBT, cervi cornu parvum, and astragali radix extracts were administered compared to the hG-CSF control group.

The hG-CSF control group exhibited a 713.41% change in the number of CD34 immunoreactive cells in the spleen compared to the normal media control group, and the groups to which 200 mg/kg of PMT, SCGBT, astragali radix, cervi cornu parvum, and angelicae gigantis radix extracts were administered exhibited changes of 30.88, 3.22, 10.04, −5.92, and 20.39%, respectively, compared to the hG-CSF control group.

The hG-CSF control group exhibited a 305.26% change in the number of CD34 immunoreactive cells in the bone marrow compared to the normal media control group, and the groups to which 200 mg/kg of PMT, SCGBT, astragali radix, cervi cornu parvum, and angelicae gigantis radix extracts were administered exhibited changes of 60.61, −10.61, 6.93, −8.87, and 75.32%, respectively, compared to the hG-CSF control group.

7.2. Numerical Changes in CD45 Immunoreactive Cells in Spleens and Bone Marrow

Figure 10:
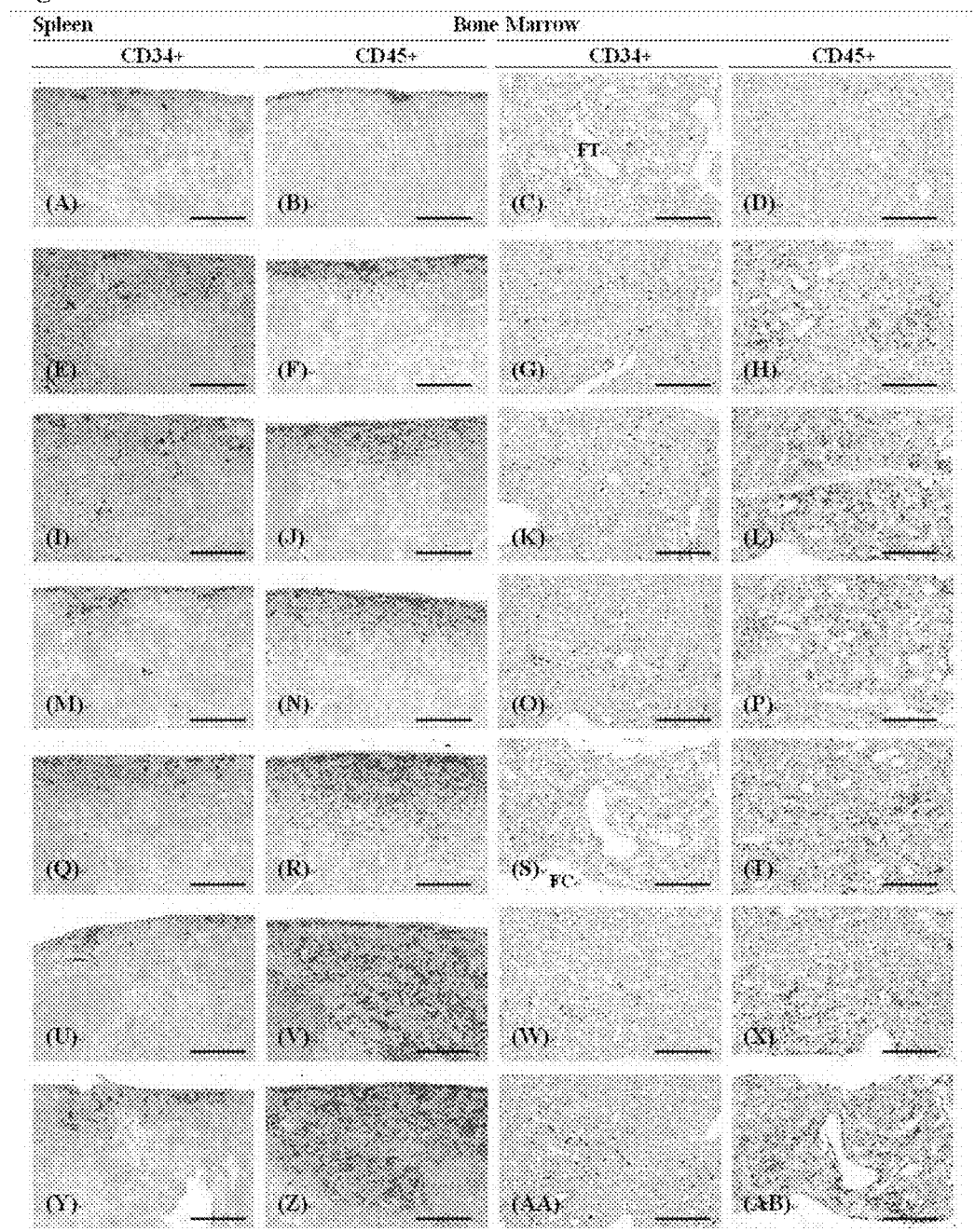
FIG. 10 is a view illustrating observations of a numerical increase in CD45 immunoreactive cells in the spleens and the bone marrow of the mice to which the hG-CSF or the natural product derived candidate substance was administered (A-D: untreated, E-H: hG-CSF, I-L: palmultang+hG-CSF, M-P: samchulgeonbitang+hG-CSF, Q-T: astragali radix+hG-CSF, U-X: cervi cornu parvum+hG-CSF, and Y-AB: angelicae gigantis radix+hG-CSF).

As can be seen in Table 9 and FIG. 10, the hG-CSF control group showed a significant (p<0.01) numerical increase in CD45 immunoreactive cells in spleens and bone marrow compared to the normal media control group, and the groups to which PMT and angelicae gigantis radix extracts were administered showed significant (p<0.01) numerical increases in CD45 immunoreactive cells in the spleens and the bone marrow even when compared to the hG-CSF control group. Meanwhile, although a significant (p<0.01) numerical increase in the CD45 immunoreactive cells in the spleen was seen in the cervi cornu parvum extract administration group compared to the hG-CSF control group, the CD45 immunoreactive cells in the bone marrow were observed to be similar with the hG-CSF control group, and no significant numerical changes in CD45 immunoreactive cells per unit area of the spleens and the bone marrow were seen in the groups to which SCGBT and astragali radix extracts were administered compared to the hG-CSF control group.

The hG-CSF control group exhibited a 575.95% change in the number of CD45 immunoreactive cells in the spleen compared to the normal media control group, and the groups to which 200 mg/kg of PMT, SCGBT, astragali radix, cervi cornu parvum, and angelicae gigantis radix extracts were administered exhibited changes of 33.51, −0.99, 7.91, 57.26, and 52.36%, respectively, compared to the hG-CSF control group.

The hG-CSF control group exhibited a 808.94% change in the number of CD45 immunoreactive cells in the bone marrow compared to the normal media control group, and the groups to which 200 mg/kg of PMT, SCGBT, astragali radix, cervi cornu parvum, and angelicae gigantis radix extracts were administered exhibited changes of 50.61, 7.56, 12.14, 5.84, and 64.94%, respectively, compared to the hG-CSF control group.

From the above results, it was confirmed that the co-administration of the angelicae gigantis radix extract can significantly increase the number of immunoreactive cells compared to the case in which only the G-CSF is administered.

To summarize the results of examples 2 to 7, a significant increase in the weight of spleens, an increase in total numbers of nuclear cells in blood and bone marrow, and numerical increases in CD34+ and CD45+ cells in the blood and the bone marrow were seen, increases in total thicknesses of spleens and numerical increases in nuclear cells per unit area of red pulp and femoral bone marrow were seen in a histopathological aspect, and numerical increases in CD34 and CD45 immunoreactive cells in the spleens and the bone marrow were seen in an immunohistochemical aspect.

Consequently, by the oral co-administration of the angelicae gigantis radix extract within five minutes of administration of the hG-CSF, proliferation and mobilization of bone marrow derived stem cells by the hG-CSF were significantly ($p<0.01$) increased, an increase in the weights of spleens and features of splenomegaly due to proliferation of nuclear cells in red pulp were significantly ($p<0.01$) suppressed, and proliferation of overall granulocytes was not affected.

Meanwhile, although significant proliferation and mobilization of the bone marrow derived stem cells were also seen in the cervi cornu parvum extract administration group, the features of splenomegaly actually worsened. Administering the SCGBT and the astragali radix extracts was observed not to affect granulocytes of hG-CSF and proliferation and mobilization of the bone marrow derived stem cells, and was also observed not to affect side effects such as splenomegaly.

Consequently, the angelicae gigantis radix extract is expected to provide a new method of fusing western and oriental medicine which is very useful in enhancing an effect of hG-CSF in mobilizing the bone marrow derived stem cells and mitigating side effects such as splenomegaly.

The above description of the present invention is for illustrative purposes, and those of ordinary skill in the art will be able to understand that the examples of the present invention may be easily modified in other specific forms without changing the technical spirit or essential characteristics of the present invention. Therefore, the above-described examples should be construed as being illustrative in every aspect, not limitative.

The invention claimed is:

1. A method for promoting proliferation of bone marrow derived stem cells comprising:
   administering a composition consisting essentially of granulocyte colony-stimulating factor and a composition consisting essentially of an angelicae gigantis radix extract to a subject in need thereof,
   wherein the stem cells are CD34+ cells.

2. The method of claim 1, wherein the stimulating factor and the angelicae gigantis radix extract are mixed in advance and made into a dosage form, or separately made into a dosage form.

3. The method of claim 1, wherein the stimulating factor and the angelicae gigantis radix extract are administered parenterally, orally, locoregionally, or percutaneously.

4. The method of claim 1, wherein the angelicae gigantis radix extract is administered within thirty minutes after administration of the stimulating factor.

* * * * *